(12) United States Patent
Vonwiller et al.

(10) Patent No.: US 8,877,243 B2
(45) Date of Patent: Nov. 4, 2014

(54) CROSS-LINKED POLYSACCHARIDE COMPOSITION

(71) Applicant: Ultraceuticals R&D Pty. Limited, Glebe (AU)

(72) Inventors: Simone Charlotte Vonwiller, Lane Cove (AU); Geoffrey Kenneth Heber, Annandale (AU)

(73) Assignee: Ultraceuticals R&D Pty., Ltd., Randwick, NSW (AU)

( * ) Notice: Subject to any disclaimer, the term of this patent is extended or adjusted under 35 U.S.C. 154(b) by 0 days.

(21) Appl. No.: 14/141,018

(22) Filed: Dec. 26, 2013

(65) Prior Publication Data

US 2014/0105852 A1    Apr. 17, 2014

Related U.S. Application Data

(63) Continuation of application No. 10/552,881, filed as application No. PCT/AU2004/000509 on Apr. 16, 2004, now abandoned.

(30) Foreign Application Priority Data

Apr. 17, 2003    (AU) ................. 2003901834

(51) Int. Cl.
| | |
|---|---|
| A61K 9/14 | (2006.01) |
| B29B 9/00 | (2006.01) |
| B29B 15/00 | (2006.01) |
| B29C 71/00 | (2006.01) |
| B29C 67/24 | (2006.01) |
| C07H 1/00 | (2006.01) |
| C08B 37/00 | (2006.01) |
| C12P 19/04 | (2006.01) |
| A61K 47/36 | (2006.01) |
| C08B 37/08 | (2006.01) |
| A61K 31/738 | (2006.01) |

(52) U.S. Cl.
CPC ............. *A61K 47/36* (2013.01); *C08B 37/0072* (2013.01); *A61K 31/738* (2013.01)
USPC .............. 424/488; 264/236; 264/330; 264/5; 264/233; 264/234; 536/123.1; 536/124; 536/126

(58) Field of Classification Search
None
See application file for complete search history.

(56) References Cited

U.S. PATENT DOCUMENTS

| | | | |
|---|---|---|---|
| 4,582,865 A | | 4/1986 | Balazs et al. |
| 4,772,419 A | * | 9/1988 | Malson et al. ............... 516/103 |
| 4,963,666 A | * | 10/1990 | Malson .................. 536/55.1 |
| 5,411,874 A | | 5/1995 | Ellwood et al. |
| 5,676,964 A | | 10/1997 | Della Valle et al. |
| 5,690,961 A | | 11/1997 | Nguyen |
| 5,827,937 A | | 10/1998 | Bengt |
| 6,852,255 B2 | | 2/2005 | Yang et al. |
| 6,852,555 B1 | * | 2/2005 | Roman et al. ............... 438/22 |
| 2003/0094719 A1 | * | 5/2003 | Yang et al. ................. 264/41 |

FOREIGN PATENT DOCUMENTS

| | | | | |
|---|---|---|---|---|
| CA | 1315464 A1 | 3/1993 | | |
| CA | 2416504 A1 | 7/2001 | | |
| EP | 0 138 572 A2 | 4/1985 | | |
| EP | 0 628 284 A1 | 12/1994 | | |
| FR | 2 717 815 A1 | 3/1994 | | |
| GB | 2 151 244 A | 7/1985 | | |
| JP | 05140201 A | 6/1993 | | |
| WO | WO 87/07898 | * | 12/1987 | ............. C08B 37/00 |
| WO | WO 00/46253 | 8/2000 | | |
| WO | WO 02/38614 | 5/2002 | | |

OTHER PUBLICATIONS

Bitter et al. *Analytical Biochemistry*. 4:330-334 (1962).
Tomihata et al. *Biomaterials*, 18:189-195 (1997).
Zhao et al. *Journal of Materials Science: Materials in Medicine*, 13:11-16 (2002).
Merriam-Webster Online Dictionary entry for the term "Reconstitute" dated Aug. 20, 2008.

* cited by examiner

*Primary Examiner* — Jeffrey T Palenik
(74) *Attorney, Agent, or Firm* — Knobbe Martens Olson & Bear LLP (57) ABSTRACT

A process for making cross-linked polysaccharide gels, particularly cross-linked hyaluronic acid gels, under basic conditions. The resulting gels possess improved degradation characteristics, and are useful in a variety of medical and cosmetic applications.

36 Claims, 3 Drawing Sheets

CROSS-LINKED POLYSACCHARIDE COMPOSITION

RELATED APPLICATIONS

The present application is a continuation of U.S. patent application Ser. No. 10/552,881, filed Jul. 17, 2006, which is the US National Phase of PCT/AU2004/000509 filed Apr. 16, 2004, which claims priority to Australian Provisional Patent Application No 2003901834, filed Apr. 17, 2003. The entire contents of all of the above-referenced applications are hereby incorporated by reference.

TECHNICAL FIELD

The present invention relates to cross-linked polysaccharide compositions, processes for preparing the compositions, and uses of the compositions in cosmetic, medical and pharmaceutical applications.

BACKGROUND ART

Hyaluronic acid (HA) is a member of a class of polymers known as glycosaminoglycans. HA is a long chain linear polysaccharide and is usually present as a sodium salt having the molecular formula $(C_{14}H_{20}NNa_{11})_n$ where n may vary according to the source of the HA and the method of isolating the HA. Molecular weights of HA of up to $14 \times 10^6$ have been reported.

HA and its salts may be isolated from many sources including the human umbilical cord, rooster combs and nearly all connective matrices of vertebrate organisms. HA is also a capsular component of bacteria such as streptococci and may therefore be obtained by fermentation methods such as reported in U.S. Pat. No. 5,411,874 (Fermentech Ltd).

HA is non-immunogenic and therefore has great potential in medicine. Because of its visco-elastic properties, HA having a high molecular weight (over 1 million) has been found to be particularly useful in a variety of clinical fields, including wound treatment, ophthalmic surgery, orthopedic surgery and drug delivery. HA is also potentially useful in a variety of non-medical fields, including cosmetic applications.

However, one drawback to administering HA to humans is that HA is degraded by enzymes such as hyaluronidase and free radicals found in the human body. Furthermore, HA is soluble in water at room temperature, which may also make it less suited to certain applications.

Various attempts have been made to prepare more stable forms of HA, in particular, by cross-linking the HA molecules. For example, hydroxyl groups have been cross-linked via an ether linkage and carboxyl groups via an ester linkage. HA has been cross-linked at pH levels less than 9 at which ester bonds form via carboxyl groups, and at pH levels greater than 9 at which ether bonds form via hydroxyl groups. The present inventors have found that ether bonds may be beneficial because these bonds are more resistant to physiological degradation.

A number of documents report a variety of methods of cross-linking HA gels. For example, U.S. Pat. No. 4,582,865 (Biomatrix Inc) reports cross-linked gels of HA formed by cross-linking HA (either by itself or mixed with other hydrophilic polymers) using divinyl sulfone as the cross-linking agent.

U.S. Pat. No. 5,827,937 (Agerup) reports polysaccharide gel compositions prepared by forming an aqueous solution of the polysaccharide, initiating cross-linking in the presence of a polyfunctional cross-linking agent, sterically hindering the cross-linking reaction from being terminated before gelation occurs (e.g. by diluting the solution) and then reintroducing sterically unhindered conditions (e.g. by evaporating the solution) so as to continue the cross-linking such that a viscoelastic gel is formed. The cross-linking in this method may be performed under alkaline or acidic conditions.

WO 00/46253 (Fermentech Ltd) reports cross-linking HA with other polymers by two different types of cross-linking bonds. The formation of different types of bonds is achieved by cross-linking via different functional groups. For example, one type of bond may be formed by cross-linking via hydroxyl groups, and a different functional bond may be formed by cross-linking via carboxyl groups.

WO 87/07898 reports reacting a polysaccharide with a polyfunctional epoxide, removing excess epoxide and employing a drying operation to cross-link the polysaccharide into a film, powdered material or similar dry product.

U.S. Pat. No. 4,963,666 (Pharmacia) reports a process in which a polysaccharide is monosubstituted with a cross-linking agent at low concentration under alkaline conditions to form ether linkages. The mixture is washed to pH 5.5 inducing some ester linkages and then, in one example, concentrated by slow evaporation to complete cross-linking with ester linkages. In another example, the pH is increased by the addition of ammonia, and then slowly evaporated to complete the cross-linking with primarily ether linkages and some ester linkages.

Although attempts have been made to improve the properties of cross-linked HA, it would be beneficial to provide cross-linked HA gels having improved degradation characteristics when administered to a patient.

DISCLOSURE OF INVENTION

In one embodiment, the present invention provides a process for producing a cross-linked polysaccharide gel. First, a polysaccharide mixed with an alkaline medium is contacted with a bifunctional or polyfunctional epoxide to form an essentially epoxy cross-linked polysaccharide in which the epoxide is linked to the polysaccharide substantially by ether bonds. The epoxy cross-linked polysaccharide is then dried without removing the epoxide from the alkaline medium. The resulting dried cross-linked polysaccharide matrix may then be washed in a suitable water miscible solvent, and treated with an acidic medium to form a cross-linked polysaccharide gel.

A variety of polysaccharide starting materials may be used in embodiments of the present invention. Suitable polysaccharides include HA, pectin, xanthan or alginic acid, as well as anionic derivatives of carboxymethyl cellulose, carboxymethyl dextran or carboxymethyl starch. HA may be a particularly suitable starting material. Suitable epoxides for use as the cross-linking agent include 1,4-butanediol ether, 1,2-ethanediol diglycidyl ether and/or epoxy-substituted pentaerythritol. It will be appreciated, however, that other epoxides may also be suitable for the present invention.

In another embodiment, the present invention provides a cross-linked polysaccharide gel prepared by the process reported herein. The gel may have improved degradation characteristics when administered to a patient.

In yet another embodiment, the present invention provides a biocompatible gel including HA cross-linked substantially by ether bonds with 1,4-butanediolglycidyl ether that is sufficiently cross-linked to resist degradation.

As used herein, the phrase "sufficiently cross-linked to resist degradation" means that the gel is relatively stable to hyaluronidase attack under physiological conditions over prolonged periods or can tolerate extrusion or being expelled from a small gauge needle. In one embodiment, the present inventors have been able to produce biocompatible gels which release less than 75 percent uronic acid when 0.4 ml of the gel having a concentration of 15 mg/ml is combined with 0.5 mg hyaluronidase and 3 ml phosphate buffered saline, and stored at a temperature of at least 37° C. for two days. Uronic acid release may be measured by the UV absorbance techniques reported in the Examples. In certain embodiments, the gels may release no more that 70 percent uronic acid, more particularly no more that 65 percent uronic acid under the foregoing conditions.

In a first aspect, the present invention provides a process for producing a cross-linked polysaccharide gel comprising:
(a) contacting a polysaccharide mixed in an alkaline medium with a bifunctional or polyfunctional epoxide to provide an essentially epoxy cross-linked polysaccharide wherein the epoxide is substantially linked to the polysaccharide by ether bonds;
(b) drying the epoxy cross-linked polysaccharide without substantially removing epoxide from the alkaline medium to form a cross-linked polysaccharide matrix;
(c) optionally washing the cross-linked polysaccharide matrix with a water miscible solvent; and
(d) neutralising the cross-linked polysaccharide matrix with an acidic medium to form a cross-linked polysaccharide gel.

In a second aspect, the present invention provides a cross-linked polysaccharide gel substantially resistant to hyaluronidase degradation prepared by the process according to the first aspect of the present invention.

In a third aspect, the present invention provides a biocompatible gel comprising hyaluronic acid cross-linked substantially by ether bonds with 1,4-butanediol diglycidyl ether such that the gel is sufficiently cross-linked to substantially resist degradation.

In a fourth aspect, the present invention provides a pharmaceutical composition comprising a cross-linked polysaccharide gel according to the second aspect of the present invention; a biologically active substance; and a pharmaceutically acceptable carrier.

In a fifth aspect, the present invention provides a pharmaceutical composition comprising a biocompatible gel according to the third aspect of the present invention; a biologically active substance; and a pharmaceutically acceptable carrier.

In a sixth aspect, the present invention provides a method of treating or preventing a disorder in a subject in need thereof, comprising administering a therapeutically effective amount of a gel according to the fourth aspect of the present invention.

In a seventh aspect, the present invention provides a method of treating or preventing a disorder in a subject in need thereof, comprising administering a therapeutically effective amount of a pharmaceutical composition according to the fifth aspect of the present invention.

In a eighth aspect, the present invention provides use of a gel according to the third aspect of the present invention in the manufacture of a medicament for treating or preventing a disorder in a subject in need thereof.

In a ninth aspect, the present invention provides use of a pharmaceutical composition according to the fourth aspect of the present invention in the manufacture of a medicament for treating or preventing a disorder in a subject in need thereof.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the present invention may be more clearly understood, preferred embodiments will be described with reference to the following drawings and examples.

MODE(S) FOR CARRYING OUT THE INVENTION

In one embodiment, the present invention provides a process for making a polysaccharide cross-linked gel. The process generally includes the steps of:
(a) forming an epoxy cross-linked polysaccharide by contacting a polysaccharide starting material with a bifunctional or polyfunctional epoxide in an alkaline medium to form an essentially cross-linked polysaccharide in which the epoxide is substantially linked to the polysaccharide by ether bonds;
(b) drying the epoxy cross-linked polysaccharide without substantially removing epoxide from the alkaline medium;
(c) optionally washing the dried epoxy cross-linked polysaccharide with a water miscible solvent to form a cross-linked polysaccharide matrix; and
(d) neutralising the epoxy cross-linked polysaccharide with an acidic medium to form a cross-linked polysaccharide gel.

Advantageously, it has been determined that when the epoxide cross-linked polysaccharide gel is formed in the foregoing manner, the gel has improved resistance to degradation when compared to conventional cross-linked polysaccharide gels.

The polysaccharide starting material may be selected from a wide range of suitable naturally-occurring carbon/late-containing polysaccharides, including HA, pectin, xanthan, or alginic acid, as well as anionic derivatives of neutral polysaccharides such as carboxymethyl cellulose, carboxymethyl dextran or carboxymethyl starch.

In one embodiment, HA is used as the polysaccharide starting material. HA may be extracted from a number of sources, for example, cocks' combs. In certain embodiments, it may be desirable to use hyaluronic acids constituting molecular fractions of the integral acids obtained directly by extraction of organic materials with a wide range of molecular weights. These fractions may be obtained by various conventional procedures, including hydrolysis, oxidation, enzymatic chemical agents or physical procedures such as mechanical or irradiation procedures. Separation and purification of the molecular fractions obtained may be accomplished by molecular filtration. An example of a suitable purified HA fraction is the "noninflammatory-NIF-NaHA sodium hyaluronate", reported by Balazs in the pamphlet "Healon"—A guide to its use in Ophthalmic Surgery—D. Miller & R. Stegmann, eds. John Wiley & Sons N.Y. 81983: p. 5.

Other suitable HA starting materials include "Hyalastine" brand and "Hyalectin" brand HA. The fraction Hyalastine has an average molecular weight of about 50,000 to 100,000 while the fraction Hyalectin has an average molecular weight of about 500,000 to 730,000. A combined fraction of these two fractions has also been isolated and characterized as having an average molecular weight of between about 250,000 and about 350,000. This combined fraction may be obtained with a yield of 80% of the total hyaluronic acid available in the particular starting material, while the fraction Hyalectin may be obtained with a yield of 30% and the fraction Hyalastine with a yield of 50% of the starting HA. The preparation of these fractions is reported in European patent publication No. 0138572A3. Other suitable HA starting materials include the fibrous and powdered HA materials reported in the Examples below.

The polysaccharide may be cross-linked by a variety of suitable polyfunctional cross-linking epoxides, including bi- or polyfunctional epoxides, such as lower aliphatic epoxides or their corresponding epihalohydrins. Specific examples of suitable epoxides include 1,4-butanediol diglycidyl ether (BDDE), 1,2-ethanediol diglycidyl ether, epoxy-substituted pentaerythritol (e.g. SHELL 162) and epihalohydrins thereof. In one embodiment, the poly-functional cross-linking agent includes 1,4-butanediol diglycidyl ether.

The polysaccharide starting material may be combined with the cross-linking agent in an alkaline medium. In one embodiment, between about 1 and about 5 w/v percent, more particularly about 4 w/v percent, polysaccharide may be added to the alkaline medium. The alkaline medium may be formed with sodium hydroxide or other suitable basic materials. The concentration of sodium hydroxide or other basic material may be between about 0.1 and about 1 w/v percent, more particularly about 1% of the total mixture. The cross-linking agent may be added to the alkaline mixture to produce a cross-linking agent concentration between about 0.05 and about 0.5%, more particularly about 0.1%. The alkaline medium may have a pH between about 9 and 12, more particularly, about 9.

The resulting alkaline mixture may be incubated under conditions that promote cross-linking of the polysaccharide with the epoxide. For example, the mixture may be incubated in a water bath at about 45° C. for about 2 hours. HA cross-linked under these conditions will substantially include ether bonds which are generally more resistant to physiological degradation than ester bonds formed under acidic conditions.

After incubation, the cross-linked mixture may be dried by conventional methods to form a polysaccharide matrix. For example the cross-linked mixture may be dried by stirring the mixture vigorously and removing the water under high vacuum for about 1.5 hours at between about 35° C. and 45° C. After drying, the polysaccharide matrix may be washed with a water miscible solvent, for example an isopropyl alcohol/water co-solvent, for several hours. Finally, the washed matrix may be neutralised with an acidic medium to form a cross-linked polysaccharide gel. For example, the matrix may be treated with a solution of 1-2 percent acetic acid in water to form the cross-linked polysaccharide gel. Optionally, the cross-linked polysaccharide gel may be further treated with a phosphate buffered saline mixture to affect the viscosity of the gel.

As further reported in the Examples below, the polysaccharide gel formed by the foregoing method is sufficiently cross-linked to resist degradation when administered to a patient. Because of the improved degradation characteristics of the gel, the resulting cross-linked polysaccharide gel may be used for a variety of applications. In one embodiment, the cross-linked polysaccharide gel may be used for augmenting tissue, treating arthritis, treating tissue adhesions, and for use in coating mammalian cells to reduce immunogenicity. In another embodiment, the cross-linked polysaccharide gel may be used in cosmetic applications, corrective implants, hormone replacement therapy, hormone treatment, contraception, joint lubrication, and ocular surgery.

Advantageously, the cross-linked polysaccharide gel remains substantially resistant to degradation following extrusion through a narrow gauge needle. Extrusion through a needle may break gels into smaller particles if the gels are not resistant to shear stress. In particular, the cross-linked polysaccharide gels of embodiments of the present invention are resistant to degradation following extrusion through a small gauge needle such as a 27, 30 or 32 gauge needle. Thus, these gels are particularly suitable for injection into tissue or skin without substantial loss of the structural integrity of the solution or gel.

In an alternate embodiment, the cross-linked polysaccharide gel may be combined with a biologically active substance for administration to a patient. Suitable biologically active substances for use with the present invention include hormones, cytokines, vaccines, cells, tissue augmenting substances, or mixtures thereof. Examples of suitable tissue augmenting substances include collagen, starch, dextranomer, polylactide, poly-beta-hydroxybutyrate, and/or copolymers thereof.

Additional examples of biologically active substances are reported in U.S. Pat. No. 5,676,964, which is incorporated herein by reference for the purpose of describing suitable biologically active substances, methods of preparing cross-linked polysaccharide gels including these substances and methods of administering the biologically active substances.

Suitable biologically active substances may include various alkaloids, peptides, phenothiazines, benzodiazepines, thioxanthenes, hormones, vitamins, anticonvulsants, antipsychotics, antiemetics, anesthetics, hypnotics, anorexigenics, tranquilizers, muscle relaxants, coronary vasodilators, antineoplastics, antibiotics, antibacterials, antivirals, antimalarials, carbonic anhydrase inhibitors, nonsteroid antiinflammatory agents, vasoconstrictors, cholinergic agonists, cholinergic antagonists, adrenergic agonists, adrenergic antagonists, narcotic antagonists.

The biologically active substance may be combined with suitable cross-linked polysaccharide gels of the present invention by physical mixing of the biologically active substance with the polysaccharide starting material. The biologically active substance may be combined in solid form, for example as a freeze-dried powder or solutions.

The use of the cross-linked polysaccharide gel as a vehicle for biologically active substances may be particularly useful in ophthalmology, where particular compatibility between the cross-linked polysaccharide gels and the corneal epithelium exists. When biologically active substances are administered in the form of concentrated solutions with elastic-viscous characteristics or in solid form on the corneal epithelium, homogenous and stable films are formed that are transparent and adhering, and that provide prolonged bioavailability of the biologically active substance. The cross-linked polysaccharide gel vehicles of embodiments of the present invention may also be suitable for treatment of diseases of the mucosa (e.g. diseases of the mount) and dermatological treatments.

In certain embodiments, the foregoing biologically active gels may be formed into pharmaceutical preparations for oral, rectal, parenteral, subcutaneous, local or intradermal use. Suitable pharmaceutical preparations may be in solid or semi-solid form, for example pills, tablets, gelatinous capsules, capsules, suppositories or soft gelatin capsules. For parenteral and subcutaneous uses, pharmaceutical preparations intended for intramuscular or intradermal uses or infusions or intravenous injections may be used, and may therefore be presented as solutions of the active compounds or as freeze-dried powders of the active compounds to be mixed with one or more pharmaceutically acceptable excipients or diluents. Additionally, pharmaceutical preparations in the form of topical preparations may be suitable, for example nasal sprays, creams and ointments for topical use or sticking plasters specially prepared for intradermal administration.

The preparations may be administered to humans or animals. In one embodiment, the cross-linked polysaccharide gel may contain between about 0.01% and 10% of biologically active substance for solutions, sprays, ointments and creams, and between about 15% and 50% of biologically active substance for the solid form preparations.

In the context of the present invention, the term "alkaline medium" includes, but is not limited to a hydroxide salt dissolved in water, preferably sodium hydroxide.

In the context of the present invention, the term "acidic medium" includes, but is not limited to an organic or inorganic acid dissolved in water, preferably acetic acid.

EXAMPLES

Synthesis of Cross-Linked Gels

Separate samples of fibrous [Javenech HTL (MW 1.6-1.33 MD)] and powder hyaluronic acid [Fluka from *Streptococcus equi* (MW 1.69 MD)] (0.5 g) were each dissolved in 1% NaOH (12.5 ml) with vigorous stirring over a period of 1 hour. 1,4-butanediol diglycidyl ether (BDDE) (12.5 µl) was added with vigorous stirring for 5 minutes and then the resulting solution was incubated without stirring in a water bath at 45° C. for 2 hours. At the end of the incubation period the mixture was removed from the bath, stirred vigorously for 1 minute and then water was removed under high vacuum for 1.5 hours at 35-40° C. The resulting transparent polysaccharide matrices were washed with an isopropyl alcohol and water mixture (IPA/H$_2$O) (6:4, 25 ml) for 22 hours, and then the IPA/H$_2$O mixture was replaced two more times every 22 hours (i.e. for a total wash time of 66 hours). The IPA/H$_2$O mixture was removed, and then 1.3 percent acetic acid in water (25 ml) was added with stirring. After 35 minutes, both samples had produced fully swollen gels with the "fibrous" gel ("Sample A") being noticeably more viscous than the "powdered" gel ("Sample B").

The gels were then subjected to a series of washes with IPA (50 ml), IPA/H$_2$O (6:4, 25 ml), IPA/H$_2$O (8:2, 100 ml), and then IPA (50 ml). The resulting opaque rubbery materials were then freeze dried to give opaque hard sheets. The sheets were then reconstituted in freshly prepared phosphate buffered saline over 24 hours at concentrations of 15 and 20 mg/ml for use in the following Examples. Sample A was pushed under pressure through a 500 µm mesh while Sample B was pushed under pressure though a 300 µm mesh. The samples were used over a 3-month period and did not degrade during storage.

Carbazole Assay

The reaction of uronic acids with carbazole is a satisfactory method to estimate the quantity of uronic acids in different compounds. The procedure reported in Bitter and Muir [T. Bitter and H. M. Muir, *Anal. Biochem.* 4, 330-334 (1962)] was followed to establish a standard titration curve.

Reagents:
- A: 0.025 M sodium tetraborate 10 H$_2$O in sulfuric acid 98%;
- B: 0.125% carbazole in absolute ethanol (stable 12 weeks at 4° C. in the dark);
- C: 11 glucuronolactone solutions of 0, 1, 5, 10, 15, 20, 25, 30, 40, 50, 75 and 100 µg/ml in deionized water saturated with benzoic acid (stable for 6 months at 4° C.).

Figure 1:
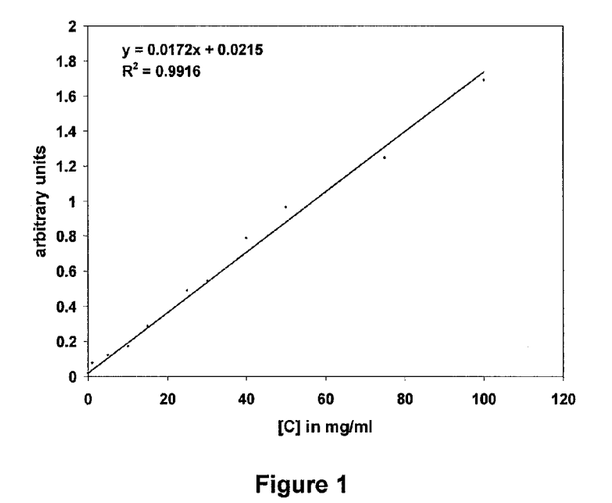
FIG. 1 shows the titration curve of hyaluronidase on a hyaluronic acid substrate as reported in the Examples.

Reagent A (5 ml) was placed in a tube and cooled to −70° C. Solution C (1 ml) was then added. The tube was sealed and allowed to warm to room temperature. The tube was then shaken and heated for 10 minutes in a vigorously boiling water bath. The tube was then cooled to room temperature. Aliquots (0.2 ml) of reagent B were then added. The tube was again shaken and heated for 15 minutes. After returning to room temperature, the UV absorption was measured at 530 nm. FIG. 1 shows a titration curve of the UV absorption values as a function of the concentration of glucuronolactone.

Resistance to Hyaluronidase of Samples A and B

To determine the concentration of uronic acid (UA) released by hyaluronidase from Samples A and B the procedure reported in X. B. Zhao, J. E. Fraser, C. Alexander, C. Lockett, B. J. White, J. Mat. Science, Materials in Medicine 13, 11-16 (2002) was followed with some modification as reported below.

Figure 2:
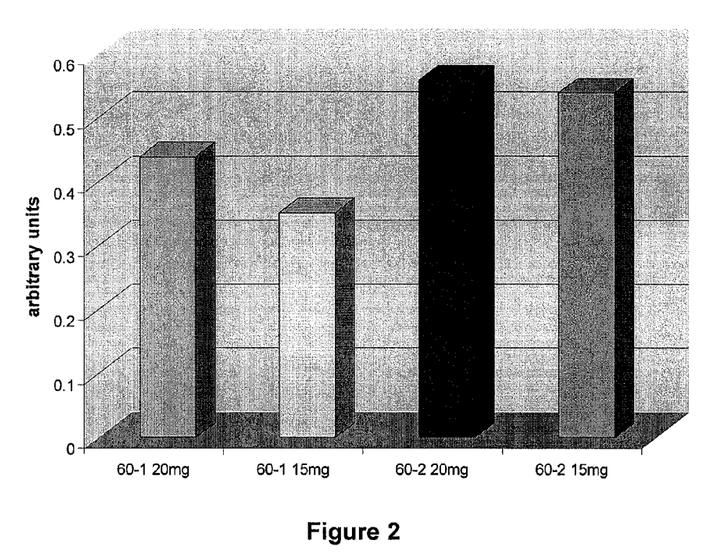
FIG. 2 shows a comparison of uronic acid (UA) release between samples A and B as reported in the Examples.

One ml of each gel at various concentrations (Sample A at 20 mg/ml, Sample A at 15 mg/ml. Sample B at 20 mg/ml and Sample B at 15 mg/ml) was suspended in 6 ml of phosphate buffered saline (pH=7.4) containing 1 mg of hyaluronidase (containing 1010 U) and incubated at 37° C. After 5 days, 0.5 ml of each Sample was diluted in 2 ml of isopropanol. The remaining gel, which was not destroyed by the enzyme, was precipitated and removed by centrifugation over 30 minutes. The supernatant liquids containing the uronic acid were then heated in a vigorously boiling bath of water for 30 minutes to denature the enzyme, and centrifuged again for 30 minutes to eliminate the enzyme. The volume of each tube was adjusted to 3.5 ml. The concentration of UA released by hyaluronidase was determined from the titration curve shown in FIG. 1 by measuring UV absorption at 530 nm. FIG. 2 shows a comparison of the different UV values.

Lower concentrations of UA were observed in gels containing a lower concentration of biopolymer (e.g. Sample A at 15 mg/ml compared to Sample A at 20 mg/ml). Also Sample A was significantly less degraded than Sample B at concentrations of both 15 and 20 mg/ml.

The concentration of UA (in µg/ml of gel solution) after 5 days of incubation was determined from the titration curve (FIG. 1). A dilution factor of 7 (i.e. 3.5/0.5) was taken into account as the 0.5 ml sample was diluted to a volume of 3.5 ml for analysis.

[UA]: concentration of UA in the gel supernatant;
[UA$_{dil}$]: concentration of UA deduced from the titration curve;
$y = 0.0172[UA_{dil}] + 0.0215$;
[UA$_{dil}$] = $(y − 0.0215)/0.0172$ where y=maximum absorption value at 530 nm;
[UA] = [UA$_{dil}$] × 7 = [(y − 0.0215)/0.0172] × 7;

Sample A, 20 mg: y=0.439, [UA]=170 µg/ml
Sample A, 15 mg: y=0.3515, [UA]=134 µg/ml
Sample B, 20 mg: y=0.559, [UA]=219 µg/ml
Sample B, 15 mg: y=0.539, [UA]=211 µg/ml Comparison of Sample A with Commercially Available Gels Restylane™ and Perlane™

A comparison between Sample A and Restylane™ gel [Q-Med AB, Uppsala, Sweden] and Perlane™ gel [Q-Med AB, Uppsala, Sweden] was performed as reported below.

Figure 3:
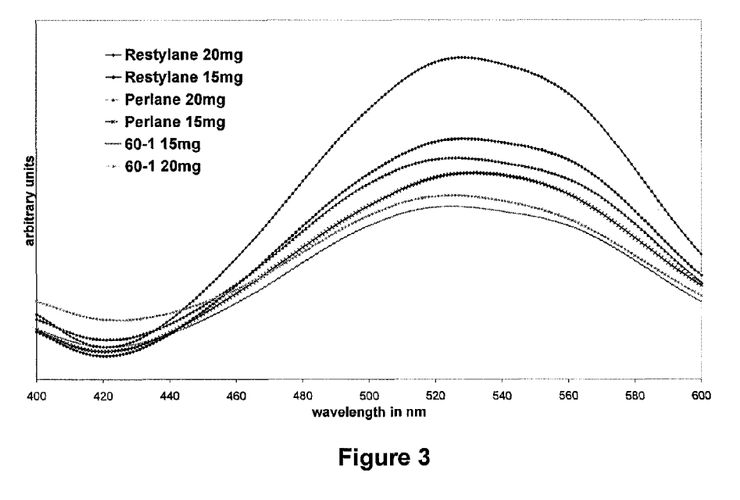
FIG. 3 shows the UV absorption of UA in gels after 1 day as reported in the Examples.

Samples (0.4 ml) of each gel were suspended in 3 ml of phosphate buffered saline (pH=7.4) containing 0.5 mg of hyaluronidase (505 U) and incubated at 37° C. The tested gels were Restylane™ gel at a concentration of 20 and 15 mg/ml, Perlane™ gel at a concentration of 20 and 15 mg/ml and Sample A at a concentration of 20 and 15 mg/ml. After 1 day, 0.25 ml of each gel was diluted in 2 ml of isopropanol. The residual gel, which was not destroyed by the enzyme, was precipitated and removed by centrifugation over 30 minutes. Each tube of gel was then heated in a vigorously boiling bath of water for 30 minutes to denature the enzyme, and centrifuged again for 30 minutes to eliminate the enzyme. The volume of each tube was adjusted to 2 ml. The concentration of UA released by hyaluronidase was determined from the titration curve by measuring UV absorption at 530 nm. The UV absorbance curve at day 1 for each gel is shown in FIG. 3.

For both the 15 mg/ml and 20 mg/ml series, Sample A exhibited improved degradation (i.e. lower concentration of UA released), when compared to Perlane™ and Restylane™ gels. Indeed Sample A at a concentration of 20 mg/ml degraded less than Perlane™ gel at a concentration of 15 mg/ml.

Effect of Needle Size on Gel Deterioration

To determine the effect of needle size on degradation of the gels, the procedure reported above was repeated on Restylane™ gel expelled or extruded through a 32G needle, Perlane™ gel expelled or extruded through a 30G needle, and Sample A (500 µm) extruded through a 32G needle and a 30G needle. Gel concentration was fixed at 15 mg/ml.

Initially, a trial experiment was run in order to establish when the maximum level of degradation of the gels was obtained in the procedure conditions (0.15 g/l of hyaluronidase).

Figure 4:
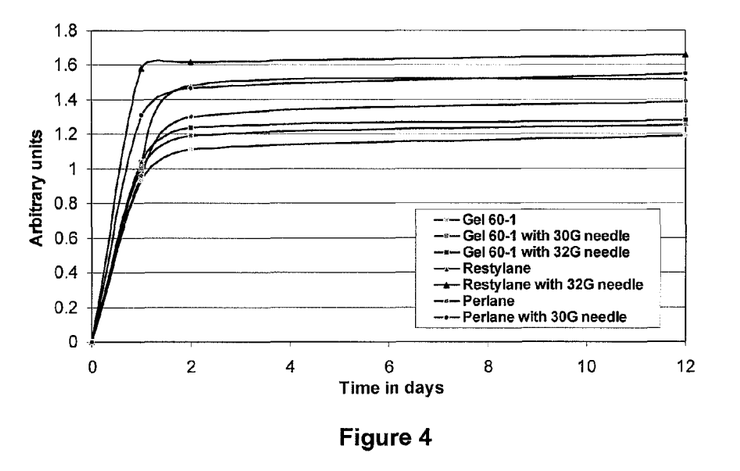
FIG. 4 shows the UV absorption of UA at 530 nm at one, two and twelve days as reported in the Examples.
Figure 5:
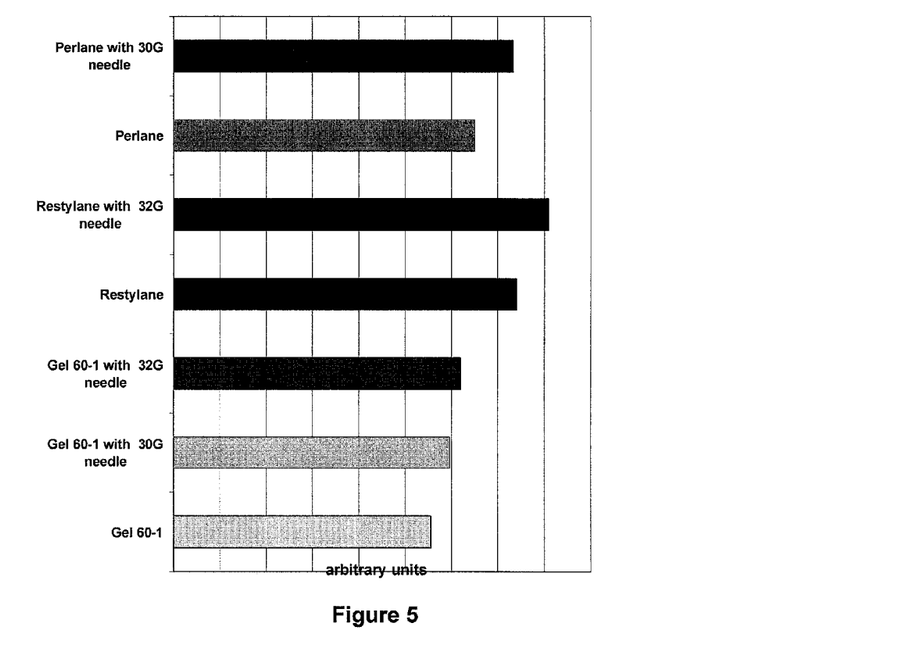
FIG. 5 shows the UV absorption of UA at 530 nm, after two days incubation as reported in the Examples.

The values obtained after two days were slightly higher than those obtained after one day. Consequently, a third set of measurements was taken after twelve days, in which the release of UA was very low compared to the first 48 hours, when the gels were mostly degraded (see FIG. 4). From this, it was determined that a two-day incubation period was sufficient to establish a comparison between the UA release (ie. degradation) of the different gels. FIG. 5, shows the UV absorption at 530 nm after two days for each experiment.

UV maxima and UA concentrations are listed in Table 1.

TABLE 1

|  | Maximum absorption (at 530 nm) | [UA] in µg/ml* |
|---|---|---|
| Sample A | 1.111 | 511 |
| Sample A, needle 30G | 1.1193 | 549 |
| Sample A, needle 32G | 1.24 | 571 |
| Restylane ™ | 1.482 | 683 |
| Restylane ™, needle 32G | 1.617 | 746 |
| Perlane ™ | 1.302 | 600 |
| Perlane ™, needle 30G | 1.466 | 676 |

*dilution factor: 2/0.25 = 8

Figure 6:
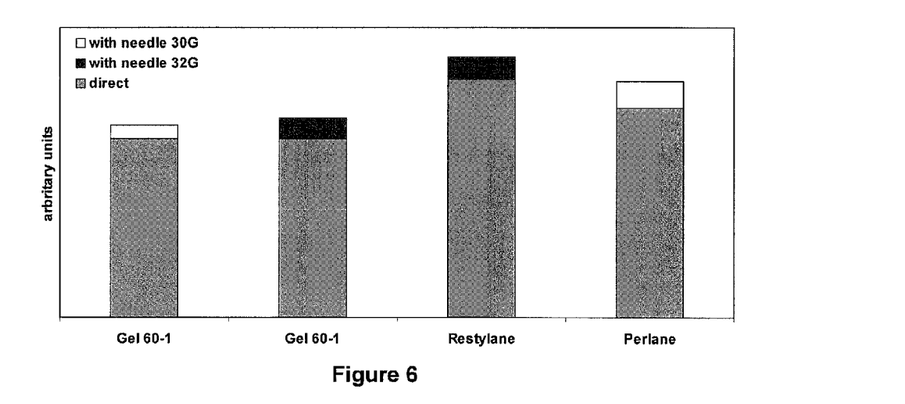
FIG. 6 shows a comparison between various gels as reported in the Examples.

Table 1 indicates that the degradation level generally increased with the decrease of the needle size. As shown in FIG. 6, even when Sample A was extruded through a 32G needle, the UA concentration remained below the values observed for both Perlane™ gel and Restylane™ gel without extrusion, thus indicating the improved degradation characteristics of Sample A.

Evaluation of the Degree of Degradation of the Gels

Initially, a maximum degradation level of each gel was established. UA extraction was performed by refluxing the gel solutions in the presence of hyaluronidase for 1 hour. Acidic treatment (see carbazole assay procedure) was applied to the 0.25 ml sample without centrifugation. Before analysis, the solution volume was adjusted to 2 ml.

The UA concentrations obtained from the UV spectra and the titration curve are presented in Table 2.

TABLE 2

|  | Maximum absorption (at 530 nm) | $[UA]_{max}$ in µg/ml* |
|---|---|---|
| Sample A | 1.6979 | 784 |
| Restylane ™ | 1.6985 | 784 |
| Perlane ™ | 1.6826 | 777 |

*dilution factor: 2/0.25 = 8

The similarity in the calculated concentrations indicates that a maximum degradation level had been reached under the reported conditions.

Next, results from Table 1 and Table 2 provided the basis to calculate the percentage of UA released in the experimental conditions listed below, relative to the maximum UA release that can be expected to measure for each gels:

% UA.=[UA]/$[UA]_{max}$×100;

Gels: 0.4 ml at 15 mg/ml;

Hyaluronidase: 0.5 mg;

Solvent: PBS, 3 ml;

TABLE 3

|  | [UA] in µg/ml* | % UA |
|---|---|---|
| Sample A | 511 | 65 |
| Sample A, needle 30G | 549 | 70 |
| Sample A, needle 32G | 571 | 73 |
| Restylane ™ | 683 | 87 |
| Restylane ™, needle 32G | 746 | 95 |
| Perlane ™ | 600 | 77 |
| Perlane ™, needle 30G | 676 | 87 |

The hyaluronidase resistance studies showed that Sample A, formed according to an embodiment of the present invention, exhibited lower degradation than the two commercially available cross-linked polysaccharide gels. It should be noted that the assay method was based on a method generally used to test dense hard gels rather than soft flowing gels, which employed a high concentration of enzyme. Consequently, all gels exhibited significant degradation after 2 days. Nevertheless, the results indicate that cross-linked polysaccharide gels formed according to embodiments of the present invention have improved degradation characteristics over commercially available gels.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A process for producing a cross-linked polysaccharide gel sufficiently cross-linked to resist degradation comprising:
   (a) contacting hyaluronic acid and at least one additional polysaccharide, mixed in an alkaline medium with a cross-linking agent consisting essentially of a bifunctional epoxide or a polyfunctional epoxide to provide an essentially cross-linked polysaccharide, wherein the cross-linking agent is substantially linked to the polysaccharide by ether bonds;
   (b) drying the cross-linked polysaccharide under vacuum without substantially removing epoxide from the alkaline medium to form a cross-linked polysaccharide matrix; and
   (c) neutralizing the cross-linked polysaccharide matrix with an acidic medium to form a cross-linked polysaccharide gel,
   wherein the cross-linked polysaccharide gel is sufficiently cross-linked by the cross-linking agent to resist degradation and wherein the alkaline medium of (a) above has a pH greater than 9.

2. The process according to claim 1, wherein the at least one additional polysaccharide is pectin, xanthan or alginic acid.

3. The process according to claim 1, wherein the at least one additional polysaccharide is selected from the group consisting of carboxymethyl dextran, carboxymethyl starch, and an anionic derivative of carboxymethyl cellulose.

4. The process according to claim 1 wherein the cross-linking agent is 1,4-butanediol diglycidyl ether, 1,2-ethanediol diglycidyl ether, or an epoxy-substituted pentaerythritol.

5. The process according to claim 4 wherein the cross-linking agent is 1,4-butanediol diglycidyl ether.

6. The process according to claim 1 wherein the alkaline medium is formed with sodium hydroxide or other basic material.

7. The process according to claim 6 wherein the alkaline medium is formed with sodium hydroxide at a concentration of between about 0.1 and about 1 w/v percent.

8. The process according to claim 1 wherein the alkaline medium comprises between 1 and 5 wt/vol percent polysaccharide and between 0.05 and 0.5 wt/vol percent epoxide.

9. The process according to claim 1 wherein the cross-linking agent contacts the polysaccharide at a temperature of at least about 45° C.

10. The process according to claim 1, the cross-linking agent contacts the polysaccharide at a temperature of about 45° C.

11. The process according to claim 1 wherein the cross-linked polysaccharide is dried under vacuum at a temperature of at least about 35° C.

12. The process according to claim 1 wherein steps (a) and (b) are performed under alkaline conditions.

13. The process according to claim 1 wherein the neutralisation step (c) further comprises freeze drying the cross-linked polysaccharide gel and reconstituting the gel.

14. The process according to claim 13 wherein the freeze dried cross-linked polysaccharide gel is reconstituted in phosphate buffered saline.

15. The process according to claim 1, further comprising, between steps (b) and (c), washing the cross-linked polysaccharide matrix with a water miscible solvent.

16. The process according to claim 15, wherein the washing step is performed under alkaline conditions.

17. The process according to claim 15 wherein the washing step comprises washing the cross-linked polysaccharide matrix with acetone.

18. The process according to claim 1, wherein the cross-linked polysaccharide gel is substantially resistant to hyaluronidase degradation.

19. The process according to claim 1 further comprising combining the polysaccharides with a biologically active substance.

20. The gel according to claim 19 wherein the biologically active substance is an alkaloid, peptide, phenothiazine, benzodiazepine, thioxanthene, hormone, vitamin, anticonvulsant, antipsychotic, antiemetic, anaesthetic, hypnotic, anorexigenic, tranquilizer, muscle relaxant, coronary vasodilator, antineoplastic, antibiotic, antibacterial, antiviral, antimalarial, carbonic anhydrase inhibitor, nonsteroid antiinflammatory agent, vasoconstrictor, cholinergic agonist, cholinergic antagonist, adrenergic agonist, adrenergic antagonist, narcotic antagonist or combination thereof.

21. A cross-linked polysaccharide gel substantially resistant to hyaluronidase degradation prepared by the process according to claim 1.

22. The gel according to claim 21 wherein the gel releases less than about 75 percent uronic acid under hyaluronidase treatment.

23. The gel according to claim 21 wherein the gel releases no more than about 70 percent uronic acid under hyaluronidase treatment.

24. The gel according to claim 21 wherein the gel releases less no more than about 65 percent uronic acid under hyaluronidase treatment.

25. The gel according to claim 21 wherein the gel releases less than about 75 percent uronic acid after being extruded or expelled from a 32 gauge needle.

26. The gel according to claim 21 wherein the gel releases no more than about 70 percent uronic acid after being extruded or expelled from a 30 gauge needle.

27. The gel according to claim 21 further comprising a biologically active substance.

28. The gel according to claim 27 wherein the biologically active substance is a hormone, cytokine, vaccine, cell, tissue augmenting substance, or mixture thereof.

29. The gel according to claim 28 wherein the tissue augmenting substance is collagen, starch, dextranomer, polylactide, poly-beta-hydroxybutyrate, or copolymers thereof.

30. The gel according to claim 27 wherein the biologically active substance is an alkaloid, peptide, phenothiazine, benzodiazepine, thioxanthene, hormone, vitamin, anticonvulsant, antipsychotic, antiemetic, anaesthetic, hypnotic, anorexigenic, tranquilizer, muscle relaxant, coronary vasodilator, antineoplastic, antibiotic, antibacterial, antiviral, antimalarial, carbonic anhydrase inhibitor, nonsteroid antiinflammatory agent, vasoconstrictor, cholinergic agonist, cholinergic antagonist, adrenergic agonist, adrenergic antagonist, narcotic antagonist or combination thereof.

31. A pharmaceutical composition comprising:
   a cross-linked polysaccharide gel substantially resistant to hyaluronidase degradation prepared by the process according to claim 1;
   a biologically active substance; and
   a pharmaceutically acceptable carrier.

32. The pharmaceutical composition according to claim 31 wherein the preparation is in the form of a pill, tablet, capsule, suppository, spray, cream, ointment or sticking plaster.

33. A method of treating a disorder or condition selected from the group consisting of tissue augmentation, arthritis, tissue adhesions, immunogenicity, diseases of the mucosa, dermatological conditions, opthalmological conditions, hormonal conditions, joint lubrication conditions, and cosmetic conditions, in a subject in need thereof, comprising administering a therapeutically effective amount of a gel substantially resistant to hyaluronidase degradation prepared by the process according to claim 1.

34. The method according to claim 33 wherein the gel further comprises a biologically active substance, and a pharmaceutically acceptable carrier.

35. The method according to claim 33, wherein the administration is by injection.

36. The method according to claim 33 wherein the administration to the subject is by topical application.

* * * * *